United States Patent [19]
Ekins

[11] Patent Number: 5,837,551
[45] Date of Patent: Nov. 17, 1998

[54] BINDING ASSAY

[76] Inventor: Roger P. Ekins, Pondweed Place, Friday Street, Abinger, Common Dorking Surrey, Great Britain, RH5 GJR

[21] Appl. No.: 663,176

[22] PCT Filed: Dec. 23, 1994

[86] PCT No.: PCT/GB94/02814

§ 371 Date: Jun. 14, 1996

§ 102(e) Date: Jun. 14, 1996

[87] PCT Pub. No.: WO95/18377

PCT Pub. Date: Jul. 6, 1995

[30] Foreign Application Priority Data

Dec. 24, 1993 [GB] United Kingdom .................. 9326450

[51] Int. Cl.$^6$ ...................................................... G01N 33/53
[52] U.S. Cl. ................. 436/518; 435/6; 435/7.1; 435/7.92; 435/962; 435/970; 435/973; 435/975; 436/518; 436/809
[58] Field of Search ................................ 435/6, 7.1, 7.92, 435/962, 970, 973, 975; 436/518, 809

[56] References Cited

U.S. PATENT DOCUMENTS

| | | | |
|---|---|---|---|
| 5,096,807 | 3/1992 | Leaback ........................................ | 435/6 |
| 5,324,633 | 6/1994 | Fodor et al. ................................. | 435/6 |
| 5,432,099 | 7/1995 | Ekins ........................................... | 436/518 |
| 5,508,200 | 4/1996 | Tiffany et al. ............................... | 436/44 |
| 5,552,272 | 9/1996 | Bogart ......................................... | 435/6 |
| 5,599,668 | 2/1997 | Stimpson et al. ............................ | 435/6 |

FOREIGN PATENT DOCUMENTS

| | | |
|---|---|---|
| 0304202 | 2/1989 | European Pat. Off. . |
| WO8401031 | 3/1984 | WIPO . |
| WO8801058 | 2/1988 | WIPO . |
| WO9308472 | 4/1993 | WIPO . |

OTHER PUBLICATIONS

Ekins et al., "Multianalyte Microspot Immunoassay—Microanalytical 'Compact Disk' of the Future," Clinical Chemistry, 37 (11):1955–67, 1991.

Berson and Yalow, "Methods in Investigative and Diagnostic Endocrinology", pp. 111–116 (1973).

*Primary Examiner*—Carol A. Spiegel
*Attorney, Agent, or Firm*—Dann, Dorfman, Herrell and Skillman

[57] ABSTRACT

The present invention provides methods for determining the concentration of analytes in liquid samples in which the amount of binding agent having binding sites specific for a given analyte in the liquid sample is immobilized in a test zone on a solid support, the binding agent being divided into an array of spatially separated locations in the test zone. The concentration of the analyte is obtained by back-titrating the occupied binding agent with a developing agent having a marker and integrating the signal from each location in the array. The present invention also provides a method for determining a value representative of a fraction of binding sites of the binding agent which are occupied by the analyte, comprising immobilizing the specific binding agent on a solid support, wherein the specific binding agent used for the fractional occupancy is present in an amount less than 0.1 V/K moles, where V is the volume of the liquid sample and K is the association constant for the analyte specifically binding to the binding agent, and wherein the specific binding agent is divided into an array of spatially separated locations; contacting the support with the liquid sample; contacting the support with the developing agent; separating non-specifically bound developing agent and measuring the signal at each of the locations to obtain a value which represents the fraction of the binding sites occupied by the analyte at each location; and adding the measured values to provide a total signal which indicates the fraction of the binding sites of the binding agent occupied by the analyte. Test kits and devices used in practicing these methods are also disclosed.

21 Claims, 3 Drawing Sheets

Minimicrospot array minimicrospot radius = r
number = N

Equivalent microspot microspot radius = R = r√N

BINDING ASSAY

This application is the U.S. national stage of PCT/GB94/02814, filed Dec. 23, 1994.

FIELD OF THE INVENTION

The present invention relates to binding assays, e.g. for determining the concentration of analytes in liquid samples.

BACKGROUND TO THE INVENTION

It is known to measure the concentration of an analyte, such as a drug or hormone, in a liquid sample by contacting the liquid with a binding agent having binding sites specific for the analyte, separating the binding agent having analyte bound to it and measuring a value representative of the proportion of the binding sites on the binding agent that are occupied by analyte (referred to as the fractional occupancy). Typically, the concentration of the analyte in the liquid sample can then be determined by comparing the fractional occupancy against values obtained from a series of standard solutions containing known concentrations of analyte.

In the past, the measurement of fractional occupancy has usually been carried out by back-titration with a labelled developing reagent using either so-called competitive or non-competitive methods.

In the competitive method, the binding agent having analyte bound to it is back-titrated, either simultaneously or sequentially, with a labelled developing agent, which is typically a labelled version of the analyte. The developing agent can be said to compete for the binding sites on the binding agent with the analyte whose concentration is being measured. The fraction of the binding sites which become occupied with the labelled analyte can then be related to the concentration of the analyte in the liquid sample as described above.

In the non-competitive method, the binding agent having analyte bound to it is back-titrated with a labelled developing agent capable of binding to either the bound analyte or the occupied binding sites on the binding agent. The fractional occupancy of the binding sites can then be measured by detecting the presence of the labelled developing agent and, just as with competitive assays, related to the concentration of the analyte in the liquid sample as described above.

In both competitive and non-competitive methods, the developing agent is labelled with a marker. A variety of markers have been used in the past, for example radioactive isotopes, enzymes, chemiluminescent markers and fluorescent markers.

In the field of immunoassay, competitive immunoassays have in general been carried out in accordance with design principles enunciated by Berson and Yalow, for instance in "Methods in Investigative and Diagnostic Endocrinology" (1973), pages 111 to 116. Berson and Yalow proposed that in the performance of competitive immunoassays, maximum sensitivity is achieved if an amount of binding agent is used to bind approximately 30 to 50% of a low concentration of the analyte to be detected. In non-competitive immunoassays, maximum sensitivity is generally thought to be achieved by using sufficient binding agent to bind close to 100% of the analyte in the liquid sample. However, in both cases immunoassays designed in accordance with these widely accepted precepts require the volume of the sample to be known and the amount of binding agent used to be accurately known or known to be constant.

In International Patent Application WO84/01031, I disclosed that the concentration of an analyte in a liquid sample can be measured by contacting the liquid sample with a small amount of binding agent having binding sites specific for the analyte. In this method, provided the amount of binding agent is small enough to have only an insignificant effect on the concentration of the analyte in the liquid sample, it is found that the fractional occupancy of the binding sites on the binding agent by the analyte is effectively independent of the volume of the sample.

This approach is further refined in EP304,202 which discloses that the sensitivity and ease of development of the assays in WO84/01031 is improved by using an amount of binding agent less than $0.1V/K$ moles located on a small area (or "microspot") of a solid support, where V is the volume of the sample and K is the equilibrium constant of the binding agent for the analyte.

In WO93/08472, I disclosed a method of further improving the sensitivity of binding assays by immobilising small amounts of binding agent at high density on a support in the form of a microspot. In this assay, a developing agent comprising a microsphere containing a marker, e.g. a fluorescent dye, is used to back-titrate the binding agent after it has been contacted with the liquid sample containing the analyte. As the microsphere can contain a large number of molecules of fluorescent dye, the sensitivity of the assay is improved as the signal from small amounts of analyte can be amplified. This amplification permits sensitive assays to be carried out even with microspots having an area of 1 $mm^2$ or less and a surface density of binding agent in the range of 1000 to 100000 molecules/$\mu m^2$.

SUMMARY OF THE INVENTION

The present invention provides a method, device and test kit for carrying out a binding assay in which binding agent having binding sites specific for a given analyte in a liquid sample is immobilised in a test zone on a solid support, the binding agent being divided into an array of spatially separated locations in the test zone, wherein the concentration of the analyte is obtained by integrating the signal from the locations in the array.

Accordingly, in one aspect, the present invention provides a method for determining the concentration of an analyte in a liquid sample comprising:

(a) locating binding agent having binding sites specific for the analyte in a test zone on a solid support, the binding agent being divided into an array of spatially separated locations;

(b) contacting the support with the liquid sample so that a fraction of the binding sites at each location become occupied by analyte;

(c) measuring a value of a signal representative of the fraction of the binding sites occupied by the analyte for each individual location in the array;

(d) integrating the signal value obtained for each location in the array to provide an integrated signal; and, (e) comparing the integrated signal to corresponding values, obtained from a series of standard solutions containing known concentrations of analyte, to determine the concentration of the analyte in the liquid sample.

Thus, in the present invention, the values of the signal from an array of locations in the test zone are used to determine the concentration of a single analyte. This is in contrast to the approach described in EP304,202, in which the signal produced at a single location is used to determine the concentration of an analyte.

The array of locations of binding agent in the test zone can be viewed sequentially, e.g. using a confocal microscope, and the signal value from each location integrated to provide the integrated signal. Alternatively, the array of locations of binding agent in the test zone can be viewed together, e.g. using a charge coupled device (CCD) camera, with the signal values from each location being measured simultaneously.

Preferably, the signals representative of the fraction of the binding sites occupied by binding agent at each location are measured by back-titrating the binding agent with a developing agent having a marker, the developing agent being capable of binding to unoccupied binding sites, bound analyte or to occupied binding sites in a competitive or non-competitive method, as described above.

The marker on the developing agent can be a radioactive isotope, an enzyme, a chemiluminescent marker or a fluorescent marker. The use of fluorescent dye markers is especially preferred as the fluorescent dyes can be selected to provide fluorescence of an appropriate colour range (excitation and emission wavelength) for detection. Fluorescent dyes include coumarin, fluorescein, rhodamine and Texas Red. Fluorescent dye molecules having prolonged fluorescent periods can be used, thereby allowing time-resolved fluorescence to be used to measure the strength of the fluorescent signal after background fluorescence has decayed. Advantageously, marker can be incorporated within or on the surface of latex microspheres attached to the developing agent. This allows a large quantity of marker to be associated with each molecule of developing agent, amplifying the signal produced by the developing agent.

Preferably, the locations are microspots and the assay is carried out using 4–40 (or more) microspots for each individual analyte, each microspot having an area less than 10000 $\mu m^2$, the microspots being separated from each other by a distance of 100–1000 $\mu m$. The locations within the array are referred to as "mini-microspots" in the relevant parts of the description that follow.

The present invention also allows the concentration of a plurality of analytes to be determined simultaneously by providing a plurality of test zones, each test zone having immobilised in it a total amount of binding agent having binding sites specific for a given analyte in a liquid sample, the binding agent being divided into an array of spatially separated locations in the test zone.

Preferably, in accordance with EP304,202, the total amount of binding agent in each array that is specific for a given analyte is less than 0.1 V/K moles, where V is the volume of the sample applied to the test zone and K is the association constant for analyte binding to the binding agent. This ensures that the "ambient analyte" conditions described in WO83/01031 are fulfilled regardless of the analyte concentration.

One way of immobilising binding agent on a support at a discrete location such as a microspot is to use technology comparable to the techniques used in ink-jet or laser printers, in the case of microspots typically providing spots having diameter of about 80 $\mu m$. Alternatively, if larger locations are required, a micropipette can be used to control the amount of binding agent immobilised at a location on a support.

The present invention is based on the observation that as the area of a microspot is reduced from a high value, such as 5 $mm^2$ towards zero, the sensitivity of the binding assay (represented by the lower limit of detection) reaches a maximum when the microspot reaches a small, but finite area, typically around 0.1 $mm^2$. Further reducing the area of microspot leads to a reduction in the sensitivity of the binding assay. However, sensitivity is enhanced by subdividing a microspot of any given area into multiple mini-microspots, such that the total coated area occupied by the mini-microspots, and hence the total amount of binding agent remains the same.

In addition, the use of an array of microspots for each individual analyte allows the user to determine whether the value obtained for any given microspot is in error by comparison with other microspots in the array.

In a further aspect, the present invention provides a device for determining the concentration of one or more analytes in a liquid sample, the device comprising a solid support having one or more test zones, each test zone having immobilised in it an amount of binding agent having binding sites specific for a given analyte in a liquid sample, the binding agent being divided into an array of spatially separated locations in the test zone, wherein the concentration of a given analyte is obtained by integrating signal values from each location in the array.

In a further aspect, the present invention provides a kit for determining the concentration of one or more analytes in a liquid sample, the kit comprising:

(a) a device comprising a solid support having one or more test zones, each test zone having immobilised in it an amount of binding agent having binding sites specific for a given analyte in a liquid sample, the binding agent being divided into an array of spatially separated locations in the test zone; and, (b) one or more developing agents for determining the fraction of the binding sites of the binding agent occupied by a given analyte, the developing agents having markers, the developing agents being capable of binding to bound analyte, or unoccupied or occupied binding sites of the binding agent;

wherein the concentration of a given analyte is obtained by integrating signal values from the markers of the developing agent at each location in the array.

BRIEF DESCRIPTION OF THE DRAWINGS

The unexpected observation of a microspot area yielding a maximum sensitivity is thought to arise because a number of opposing effects combine to produce this outcome. These effects are explained with reference to the accompanying figures in which.

DETAILED DESCRIPTION

Note that in FIGS. 1 to 4, the exact shape of the curves shown will depend on a number of parameters, including the physico-chemical properties (ie association and dissociation rate constants) of the binding agent, the viscosity of the analyte containing solution to which the microspot is exposed, the specific activity of the label used, etc.

In all the figures, value A denotes the area of a microspot typically used in the prior art (typically 1 mm$^2$). In all the figures, the density of binding agent is kept constant.

Figure 1:
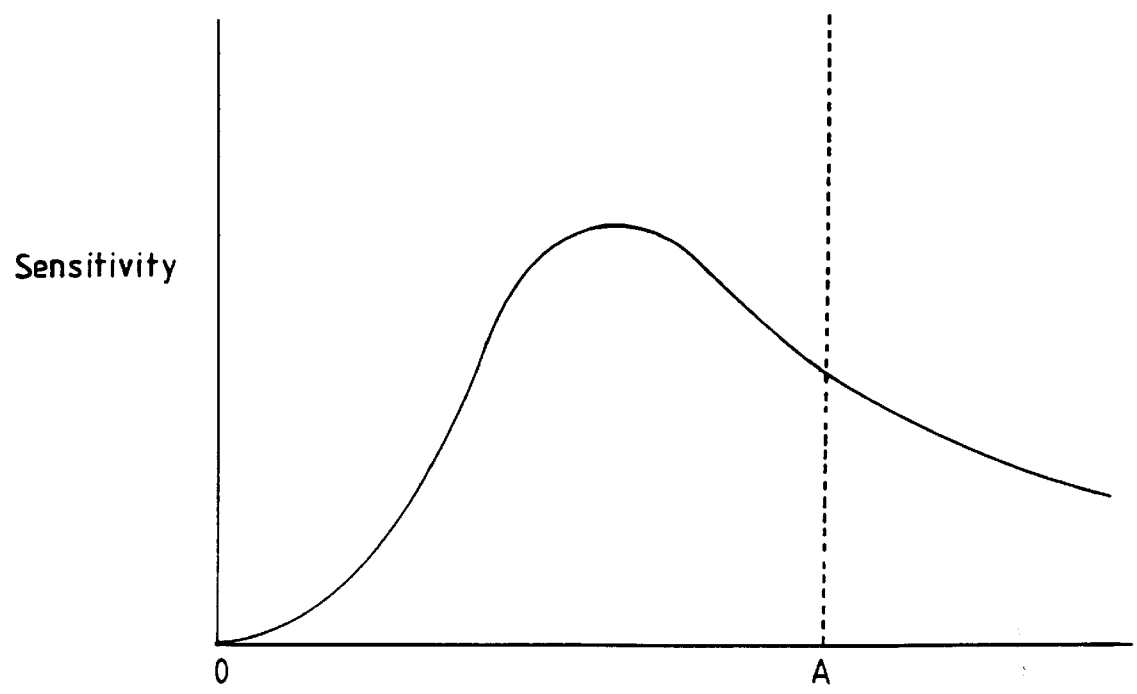
FIG. 1 represents how the sensitivity of a binding assay typically changes with area of microspot at constant binding agent density.

FIG. 1 shows the experimentally observed variation of sensitivity as the area of a microspot is reduced. In the present context, sensitivity can be defined as the lower limit of detection which is given by the error (s.d) with which it is possible to measure zero signal. As FIG. 1 shows, as the area is reduced from value A, the sensitivity of the binding assay reaches a maximum and then declines as the area of the microspot is further reduced towards zero.

Figure 2:
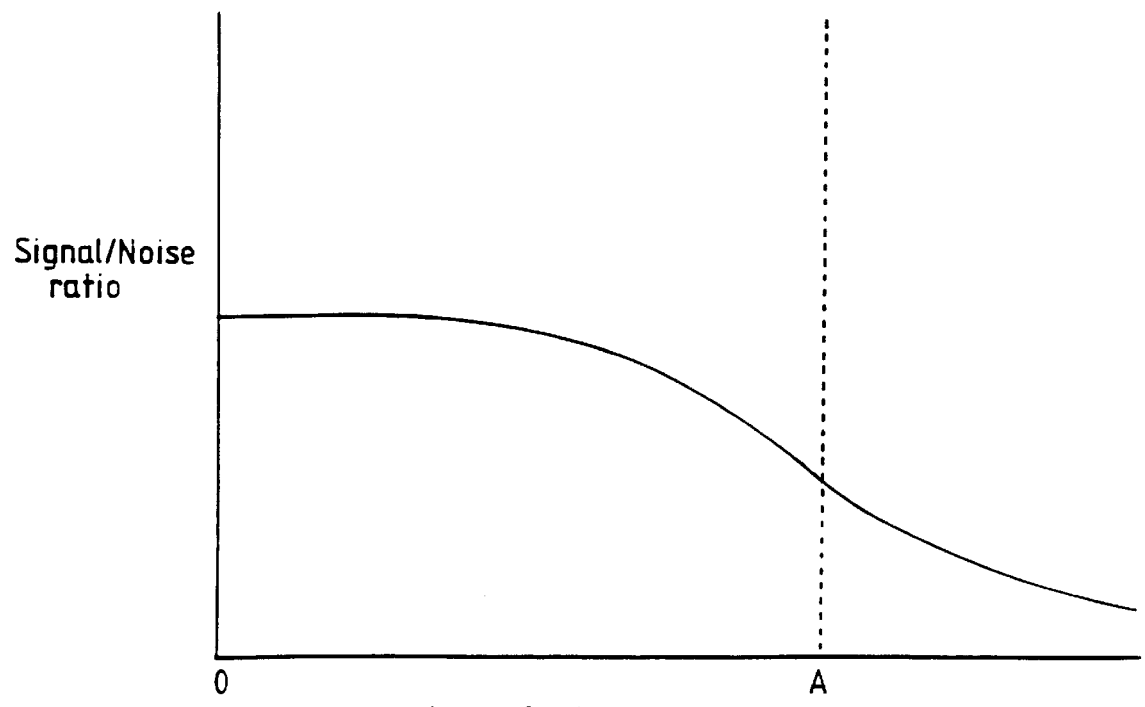
FIG. 2 represents the typical variation in signal-to-noise ratio as the area of a microspot changes.
Figure 3:
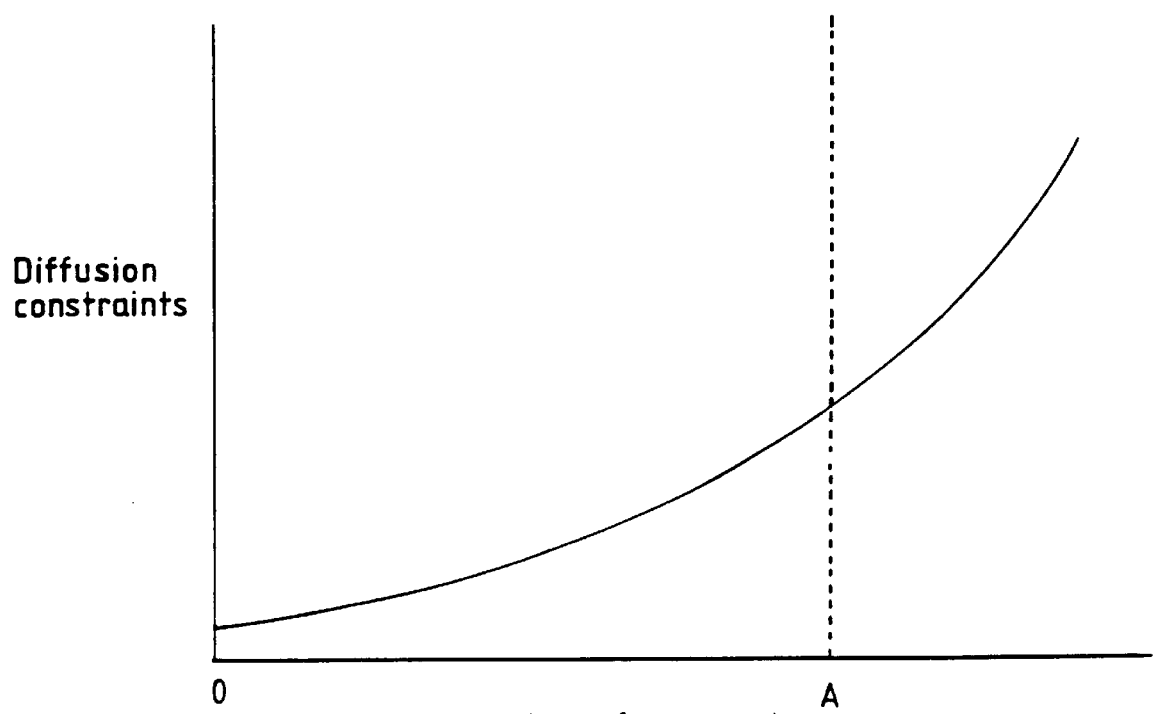
FIG. 3 represents how diffusion constraints on analyte binding to the binding agent change as the area of the microspot changes.
Figure 4:
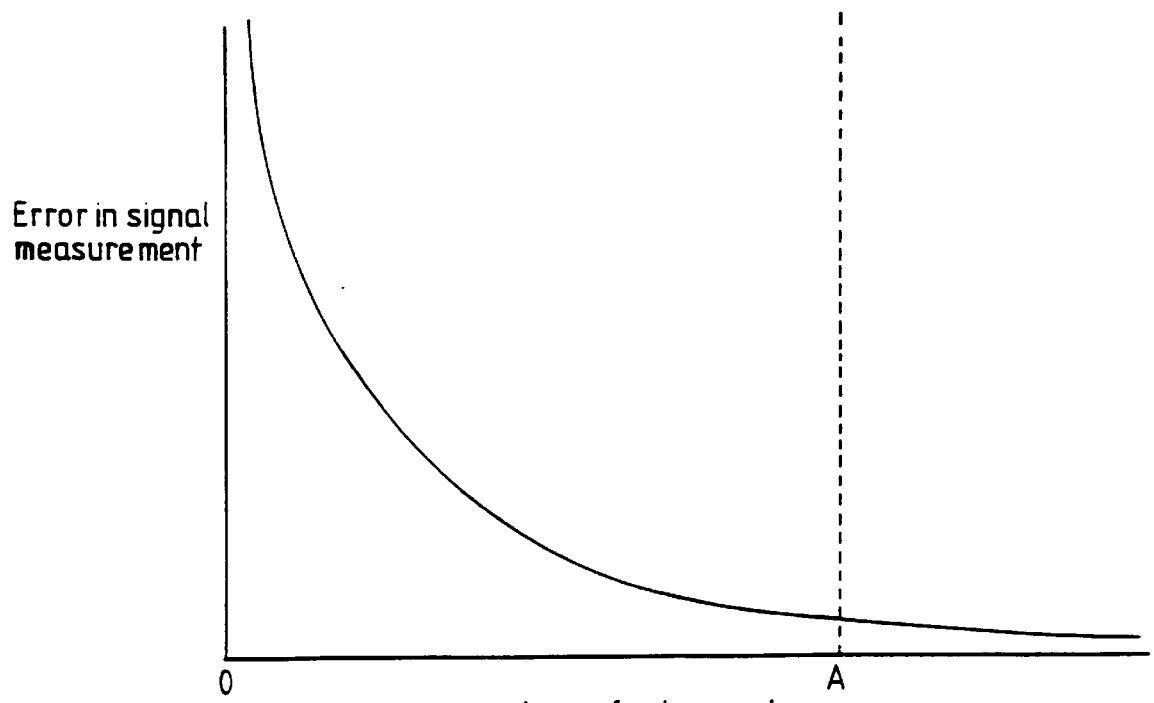
FIG. 4 shows how the error in signal measurement changes as the area of the microspot changes.

Some of the opposing factors leading to this observation are depicted in FIGS. 2 to 4.

FIG. 2 shows how the signal-to-noise ratio associated with the measurement of the occupancy of the binding sites of the binding agent changes as the size of the microspot decreases towards zero, assuming equilibrium has been reached. As microspot area is reduced from value A, the fractional occupancy of the binding sites of the binding agent reaches a plateau value as the concentration of binding agent falls below 0.01/K. Therefore, the signal per unit area from markers on developing agent used to measure the occupancy of the binding sites by analyte will also reach a plateau. As the background noise per unit area remains approximately constant, so the signal-to-noise ratio will likewise increase to a plateau value as the concentration of binding agent falls below 0.01/K.

FIG. 3 shows how diffusion constraints change as the area of a microspot is reduced. "Diffusion constraints" restrict the rate at which analyte migrates towards and binds to the binding agent. As FIG. 3 shows, the diffusion constraints decrease as microspot size decreases, ie the kinetics of the binding process are faster for smaller microspots, implying that thermodynamic equilibrium in the system is reached more rapidly.

On a molecular level, this phenomenon can be pictured as follows. When a microspot containing binding agent is placed in a liquid sample containing analyte, the binding agent binds analyte, depleting the local concentration of the analyte as compared to the liquid sample as a whole. This leads to a concentration gradient being established in the vicinity of the microspot until thermodynamic equilibrium is reached. This process is found to be slower for larger microspots the diffusion constraint being approximately proportional to microspot radius. When the occupancy of the binding sites on the binding agent has reached an equilibrium value, the concentration of analyte in the liquid sample is uniform. However, equilibrium is reached more rapidly in the case of microspots of smaller size, implying that, for any incubation time less than that required to reach equilibrium in the case of the larger spot, the fractional occupancy of the binding sites on the smaller spot is greater.

However, as microspot area decreases, so the amount of binding agent and the level of signal from developing agent will likewise decrease. This leads to an increase in the statistical errors in the measurement of the signal from a marker on a developing agent, which tend to infinity as the microspot area tends to zero (see FIG. 4).

It can be seen that a consideration of the signal-to-noise ratio and diffusion constraints indicate an increase in the sensitivity of a binding assay as the area of a microspot is decreased. However, these factors are opposed by an increase in the statistical error of signal measurement as the microspot area decreases. These factors combine to produce the observed variation of sensitivity with microspot area shown in FIG. 1. Thus, the overall consequence is that, as microspot area falls to zero, the binding assay becomes totally insensitive.

However, it is desirable to develop sensitive miniaturised binding assays using microspots of the smallest possible size containing vanishingly small amounts of binding agent, that have rapid kinetics to minimise the time taken to carry out the assay.

The present invention improves sensitivity and reduces binding assay incubation times by exploiting the contradictory effects discussed above to maximal advantage. This is done by sub-dividing the total amount of binding agent into an array of spatially separated locations such as "minimicrospots", to reduce diffusion constraints, and integrating the signals representative of the fractional occupancy of binding agent at each location to obtain a total signal greater than would have been achieved by using a single microspot equal in area to the total area occupied by the minimicrospots comprising the minimicrospot array.

This implies, inter alia, that the total amount of binding agent used can be made even smaller than in the prior art where a balance between kinetics and signal-to-noise relative to statistical errors had to be made to optimise sensitivity. The present invention therefore can improve the signal-to-noise ratio associated with measuring the analyte bound to binding agent, whilst reducing the diffusion constraints associated with each microspot in the array. Moreover, the increasing statistical errors observed in the prior art as microspot size is reduced are obviated, as the signal generated from the occupied binding sites by analyte in the individual microspots is integrated over the array to provide an integrated signal, thereby retaining the signal measurement advantage observed for larger microspots.

Figure 5:
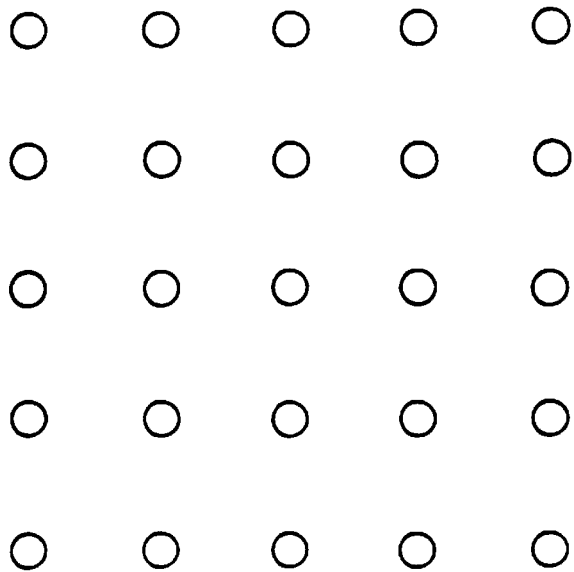
FIG. 5 shows a comparison between the microspot array of the present invention and a single microspot of the prior art.
Figure 5:
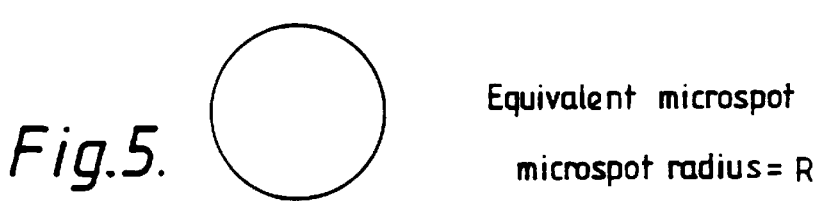

FIG. 5 illustrates how a single microspot of the prior art can be divided into an array of 25 microspots containing an equivalent total amount of binding agent.

Figure 6:
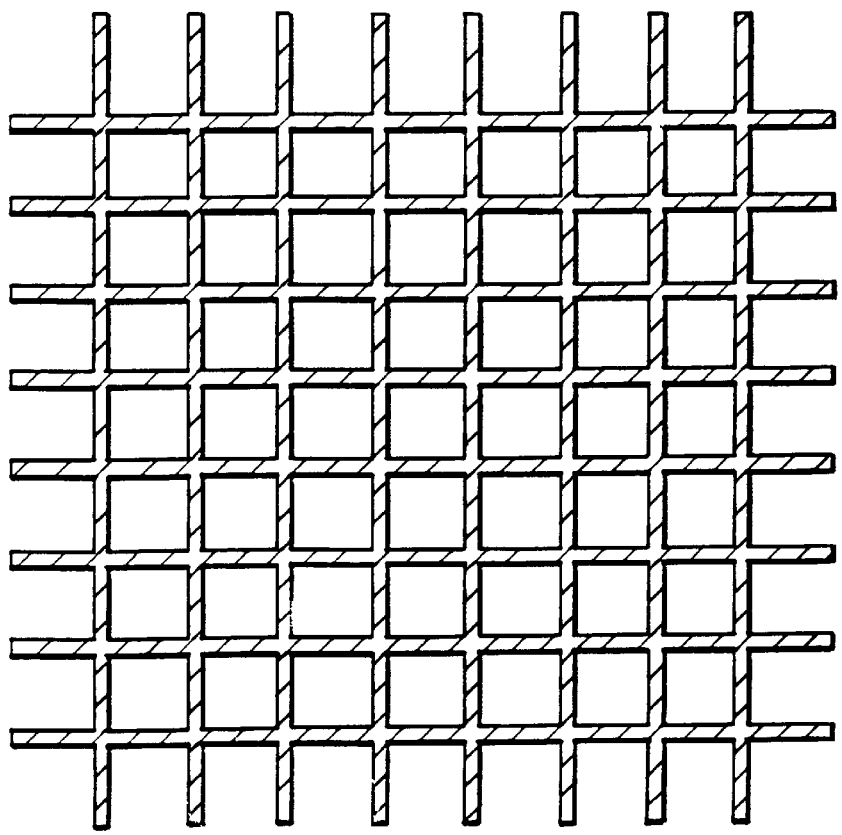
FIG. 6 shows binding agent immobilised as an array of lines in an alternative embodiment of the invention.

Nevertheless, other arrangements or geometries of binding agent providing assays yielding the same benefits can be envisaged, see for instance FIG. 6 which shows binding agent immobilised as lines forming a grid (see the shaded areas). This configuration likewise has the effect of reducing the diffusion constraints whilst maintaining the total area coated with binding agent (e.g. an antibody) to obviate the increasing statistical errors and associated loss of sensitivity observed as the amount of binding agent is reduced.

The amount and distribution of the binding agent in the locations comprising the array depends on a variety of factors including the diffusion characteristics of the analyte, the nature and viscosity of the liquid sample containing the analyte and the protocol used during incubation. However, given the guidance here the skilled person can readily determine, either experimentally or by computer modelling, the optimal arrangement or geometry of array for any given binding assay.

EXAMPLE

Conjugation of Anti-TSH (Anti-Thyroid Stimulating Hormone) Mouse Monoclonal Antibody to Fluorescent Hydrophilic Latex Microspheres 1. 10 mg of fluorescent hydrophilic latex microspheres in 0.5 ml double distilled water were added to 0.5 ml of 1% TWEEN 20, surface-active agent, shaken for 15 min at room temperature and centrifuged at 8° C. for 10 min at 20,000 rpm in a MSE High-Spin 20 ultracentrifuge.

2. The pellet was dispersed in 2 ml of 0.05M MES (2-[N-Morpholino] ethanesulfonic acid) buffer, pH6.1 and centrifuged.

3. Step 2 was repeated.

4. The pellet was dispersed in 0.8 ml MES buffer.

5. 2 mg of anti-TSH monoclonal developing antibody in 100 μl were added to the microspheres and shaken for 15 min at room temperature.

6. 100 μl of 0.25% ethyl-3 (3-dimethyl amino) propyl carbodimide hydrochloride were added to the mixture and shaken for 2 hours at room temperature.

7. 10 mg glycine in 100 μl of MES buffer were added to the mixture, shaken for a further 30 min and centrifuged.

8. The pellet was dispersed in 2 ml of 1% BSA (Bovine Serum Albumin), shaken for 1 hour at room temperature and centrifuged.

9. The pellet was dispersed in 2 ml of 1% BSA, shaken for 1 hour at room temperature and centrifuged.

10. The pellet was dispersed in 2 ml of 0.1M phosphate buffer, pH7.4 and centrifuged.

11. Step 10 was repeated twice.

12. The pellet was dispersed in 2 ml of 1% BSA containing 0.1 sodium azide and stored at 4° C.

Comparison of Kinetics of Micro Versus Mini-micro Capture Antibody Microspots in a Sandwich TSH (Thyroid Stimulating Hormone) Assay 1. Anti-TSH capture antibody microspots (diameter 1.1 mm, area=$10^6$ $\mu m^2$) were made by depositing 0.5 μl of 200 μg/ml antibody solution on each of 16 Dynatech black MicroFluor Microtitre wells, the droplets were aspirated immediately, the wells blocked with SuperBlock from Pierce for 30 min at room temperature and washed with 0.1M phosphate buffer, pH7.4.

2. The mini-microspots (diameter 0.16 mm) were made using an piezoelectric ink-jet print-head with an anti-body solution concentration of 1 mg/ml and droplets of approximately 100 pl picoliter for an array of 49 (7×7) mini-microspots per microtitre wells (total coated antibody area= $10^6$ $\mu m^2$) for 16 wells. The wells were blocked with SuperBlock and washed with phosphate buffer as above. The coated antibody density for both micro and mini-microspots are estimated to be $2 \times 10^4$ IgG/$\mu m^2$.

3. 200 μl of plasma containing 1 μU/ml of TSH was added to all the microtitre wells and shaken at room temperature. At 30, 60, 120 min and 18 hours (overnight), four wells containing the microspots and mini-microspots were washed with phosphate buffer containing 0.1% TWEEN 20, then incubated with 200 μl of anti-TSH developing antibody conjugated to hydrophilic latex microspheres in Tris-HCl buffer (50 μg/ml) for 30 min at room temperature and washed with phosphate-TWEEN 20 buffer. The wells were then scanned with a laser scanning confocal microscope equiped with an Argon/Krypton laser.

Results

| Sample incubation times (mins) | Total Fluorescent Signal (arbitrary units) | |
|---|---|---|
| | Microspot | Mini-microspot |
| 30 | 85 ± 7 | 111 ± 13 |
| 60 | 118 ± 15 | 149 ± 16 |
| 120 | 141 ± 21 | 178 ± 16 |
| Overnight | 185 ± 20 | 191 ± 23 |

Conclusion

Significantly higher mean responses were observed between 30 and 120 mins in the mini-micro spot samples, while the overnight controls did not show significant differences. This demonstrates that the mini-microspots have faster kinetic for the association of analyte with the capture antibody, and could be used to reduce incubation times.

The invention claimed is:

1. A method for determining the concentration of at least one analyte in a liquid sample, said method comprising, for each analyte, the steps of:

(a) immobilizing a specific binding agent including binding sites specific for the analyte on a solid support, wherein the specific binding agent used to determine the concentration of the analyte is present in an amount less than 0.1 V/K moles, where V is the volume of the liquid sample and K is the association constant for the analyte specifically binding to the specific binding agent, and wherein said specific binding agent is divided into an array of spatially separated locations;

(b) contacting the support with the sample so that a fraction of the binding sites of the specific binding agent specific for the analyte specifically binds the analyte;

(c) contacting the support with a developing agent labelled with a signal-producing marker such that the labelled developing agent binds to unoccupied binding sites, to specifically bound analyte or to the binding sites with specifically bound analyte;

(d) separating non-specifically bound developing agent from the solid support and measuring the signal produced by the marker at each of the locations in the array to obtain a value which represents the fraction of the binding sites occupied by the analyte at each location;

(e) adding the values obtained at the locations in the array to provide a total signal; and (f) comparing the total signal to corresponding values obtained from a series of standard solutions containing known concentrations of the analyte, to determine the concentration of the analyte in the liquid sample.

2. The method according to claim 1, wherein the specific binding agent is divided into between 4 and 40 locations.

3. The method according to claim 1, wherein the locations have an area of about 10000 $\mu m^2$, the locations being separated from each other by a distance of 100 to 1000 μm.

4. The method according to claim 1, wherein the concentration of a plurality of different analytes in the liquid sample are determined using a plurality of arrays on said support.

5. The method according to claim 1, wherein (i) the specific binding agent is an antibody and the analyte is an antigen or (ii) the specific binding agent is an oligonucleotide and the analyte is a nucleic acid.

6. A method for determining the concentration of at least one analyte in a liquid sample, said method comprising, for each analyte, the steps of:

(a) immobilizing a specific binding agent including binding sites specific for the analyte on a solid support, wherein the specific binding agent used to determine the concentration of the analyte is present in an amount less than 0.1 V/K moles, where V is the volume of the liquid sample and K is the association constant for the analyte specifically binding to the specific binding agent, and wherein said specific binding agent is divided into an array of spatially separated locations;

(b) contacting the support with the liquid sample so that a fraction of the binding sites of the binding agent specific for the analyte specifically bind the analyte;

(c) contacting the support with a developing agent labelled with a signal-producing marker such that the labelled developing agent binds to unoccupied binding sites, to specifically bound analyte or to the binding sites with specifically bound analyte;

(d) separating non-specifically bound developing agent from the solid support and measuring the signal produced by the marker at each of the locations in the array to obtain a value which represents the fraction of the binding sites occupied by the analyte at each location; and (e) adding the values obtained at the locations in the array to provide a total signal which indicates the concentration of the analyte in the liquid sample.

7. The method according to claim 6 wherein the specific binding agent is divided into between 4 and 40 locations.

8. The method according to claim 6, wherein the locations are in an area of about 10000 $\mu m^2$, the locations being separated from each other by a distance of 100 to 1000 $\mu m$.

9. The method according to claim 6, wherein the concentrations of a plurality of different analytes in the liquid sample are determined using a plurality of arrays on said support.

10. The method according to claim 6, wherein (i) the specific binding agent is an antibody and the analyte is an antigen or (ii) the specific binding agent is an oligonucleotide and the analyte is a nucleic acid.

11. A method for determining the concentration of at least one analyte in a liquid sample, said method employing a solid support on which is immobilized, for each analyte, a specific binding agent including binding sites specific for the analyte, wherein the specific binding agent used to determine the concentration of the analyte is present in an amount less than 0.1 V/K moles, where V is the volume of the liquid sample and K is the association constant for the analyte specifically binding to the specific binding agent, and wherein said specific binding agent is divided into an array of spatially separated locations, said method comprising the steps of:

(a) contacting the support with the sample so that a fraction of the binding sites of the specific binding agent specific for the analyte specifically binds the analyte;

(b) contacting the support with a developing agent labelled with a signal-producing marker such that the labelled developing agent binds to unoccupied binding sites, to specifically bound analyte or to the binding sites with specifically bound analyte;

(c) separating non-specifically bound developing agent from the solid support and measuring the signal produced by the marker at each of the locations in the array to obtain a value which represents the fraction of the binding sites occupied by the analyte at each location;

(d) adding the values obtained at the locations in the array to provide a total signal; and (e) comparing the total signal to corresponding values obtained from a series of standard solutions containing known concentrations of the analyte, to determine the concentration of the analyte in the liquid sample.

12. The method according to claim 11, wherein the specific binding agent is divided into between 4 and 40 locations.

13. The method according to claim 11, wherein the locations have an area of about 10000 $\mu m^2$, the locations being separated from each other by a distance of 100 to 1000 $\mu m$.

14. The method according to claim 11, wherein the concentrations of a plurality of different analytes in the liquid sample are determined using a plurality of arrays on said support.

15. The method according to claim 11, wherein the specific binding agent is an antibody and the analyte is an antigen.

16. The method according to claim 11, wherein the specific binding agent is an oligonucleotide and the analyte is a nucleic acid.

17. A method for determining a value representative of a fraction of binding sites of a specific binding agent including binding sites specific for an analyte which binding sites are occupied by the analyte present in a liquid sample, said method comprising the steps of:

(a) immobilizing the specific binding agent on a solid support, wherein the specific binding agent used for the fractional occupancy determination is present in an amount less than 0.1 V/K moles, where V is the volume of the liquid sample and K is the association constant for the analyte specifically binding to the specific binding agent, and wherein said specific binding agent is divided into an array of spatially separated locations;

(b) contacting the support with the liquid sample so that a fraction of the binding sites of the binding agent specific for the analyte specifically bind the analyte;

(c) contacting the support with a developing agent labelled with a signal-producing marker such that the labelled developing agent binds to unoccupied binding sites, to specifically bound analyte or to the binding sites with specifically bound analyte;

(d) separating non-specifically bound developing agent from the solid support and measuring the signal produced by the marker at each of the locations in the array to obtain a value which represents the fraction of the binding sites occupied by the analyte at each location; and (e) adding the values obtained at the locations in the array to provide a total signal which indicates the fraction of the binding sites in the specific binding agent occupied by the analyte.

18. The method according to claim 17, wherein the specific binding agent is divided into between 4 and 40 locations.

19. The method according to claim 17, wherein the locations are in an area of about 10000 $\mu m^2$, the locations being separated from each other by a distance of 100 to 1000 $\mu m$.

20. The method according to claim 17, wherein the fraction of occupied binding sites is determined for a plurality of different analytes in the liquid sample using a plurality of arrays on said support.

21. The method according to claim 17, wherein (i) the specific binding agent is an antibody and the analyte is an antigen or (ii) the specific binding agent is an oligonucleotide and the analyte is a nucleic acid.

* * * * *